(12) United States Patent
Cossu et al.

(10) Patent No.: US 8,247,460 B2
(45) Date of Patent: Aug. 21, 2012

(54) METHOD OF TREATMENT FOR MUSCULAR DYSTROPHY

(76) Inventors: Giulio Cossu, Rome (IT); Emilio Clementi, Milan (IT); Silvia Brunelli, Milan (IT)

( * ) Notice: Subject to any disclaimer, the term of this patent is extended or adjusted under 35 U.S.C. 154(b) by 411 days.

(21) Appl. No.: 12/278,100

(22) PCT Filed: Feb. 1, 2007

(86) PCT No.: PCT/EP2007/000858
§ 371 (c)(1),
(2), (4) Date: Apr. 13, 2009

(87) PCT Pub. No.: WO2007/088050
PCT Pub. Date: Aug. 9, 2007

(65) Prior Publication Data
US 2009/0304815 A1    Dec. 10, 2009

Related U.S. Application Data

(60) Provisional application No. 60/765,135, filed on Feb. 3, 2006.

(51) Int. Cl.
*A61K 31/21* (2006.01)
*A61K 31/19* (2006.01)
*A01N 59/00* (2006.01)
*A01N 37/00* (2006.01)

(52) U.S. Cl. ......... 514/907; 424/718; 514/509; 514/568

(58) Field of Classification Search .......................... None
See application file for complete search history.

(56) References Cited

U.S. PATENT DOCUMENTS 6,245,811 B1 * 6/2001 Horrobin et al. .............. 514/547

FOREIGN PATENT DOCUMENTS

WO        00/53191 A    9/2000
WO     WO 00/53191   *  9/2000

OTHER PUBLICATIONS

MedlinePlus Muscular Dystrophy [online] retrieved from: http://www.nlm.nih.gov/medlineplus/ency/article/001190.htm on Oct. 4, 2011; Mar. 9, 2010; 4 pages.*

Wang et al. Chem Rev 2002; 102; 1091-1134.*
Sciorati et al. (British Journal of Pharmacology 2010, 160, 15550-1560).*
Chiroli, V., et al., "Nitric oxide-donating non-steroidal anti-inflammatory drugs: the case of nitroderivatives of aspirin", European Journal of Medicinal Chemistry, Editions Scientifique Elsevier, Paris, FR, vol. 38, No. 4, Apr. 2003, pp. 441-446.
Armour, K. J., et al., "Inhibition of bone resorption in vitro and prevention of ovariectomy-induced bone loss in vivo by flurbiprofen nitroxybutylester (HCT1026)", Arthritis and Rheumatism, Lippincott, Philadelphia, US, vol. 44, No. 9, Sep. 2001, pp. 2185-2192.
"HCT-1026 fluribiprofen nitroxybutyl ester", Drugs of the Future, Barcelona, ES, vol. 24, No. 8, Aug. 1999, pp. 858-861.
Zacharowski, P., et al., "The effects and metabolic fate of nitroflurbiprofen in healthy volunteers", Clinical Pharmacology & Therapeutics, Mosby-Year Book, St Louis, MO, US, vol. 76, No. 4, Oct. 2004, pp. 350-358.
Ranatunge, et al., "Synthesis and anti-inflammatory activity of a series of N-substituted naproxen glycolamides: nitric oxide-donor naproxen prodrugs", Bioorganic & Medicinal Chemistry, Elsevier Science Ltd, GB, vol. 14, No. 8, Dec. 13, 2005, pp. 2589-2599.
Chaubourt, E., et al., "Nitric oxide and L-arginine cause an accumulation of utrophin at the sarcolemma: A possible compensation for dystrophin loss in duchenne muscular dystrophy", Neurobiology of Disease, Blackwell Scientific Publications, Oxford, GB, vol. 6, No. 6, 1999, pp. 499-507.
Cossu, G., et al., "New therapies for muscular dystrophy: cautious optimism", Trends in Molecular Medicine, vol. 10, No. 10, Oct. 2004, pp. 516-520.
Wang, Q., et al., "Induction of HSP70 expression and recruitment of HSC70 and HSP70 in the nucleus reduce aggregation of a polyalanine expansion mutant of PABPN1 in HeLa cells", Human Molecular Genetics, vol. 14, No. 23, Dec. 2005, pp. 3673-3684.
Brunelli, S., et al., "Nitric oxide release combined with nonsteroidal anti inflammatory activity prevents muscular dystrophy pathology and enhances stem cell therapy", Proceedings of the National Academy of Sciences of the United States of America, vol. 104, No. 1, Jan. 2, 2007, pp. 264-269.
Archer, J. D., et al., "Persistent and improved functional gain in mdx dystrophic mice after treatment with L-arginine and deflazacort", The FASEB Journal : Official Publication of the Federation of American Societies for Experimental Biology Apr. 2006, vol. 20, No. 6, Apr. 2006, pp. 738-740.

* cited by examiner

*Primary Examiner* — Ernst Arnold
(74) *Attorney, Agent, or Firm* — Lucas & Mercanti, LLP (57) ABSTRACT

The invention relates to a method of treatment for muscular dystrophies, including Duchenne, Becker, limb-girdle, facioscapulohumeral, congenital muscular dystrophies and the like using a combination of nitric oxide-releasing and anti-inflammatory compounds.

5 Claims, 6 Drawing Sheets

METHOD OF TREATMENT FOR MUSCULAR DYSTROPHY

CROSS-REFERENCE TO RELATED APPLICATIONS

This application is a 371 of PCT/EP2007/000858 filed on Feb. 1, 2007, which claims the benefit of U.S. Patent Application No. 60/765,135 filed on Feb. 3, 2006, the contents of each of which are incorporated-herein by reference.

The invention relates to a method of treatment for muscular dystrophies, including Duchenne, Becker, limb-girdle, facioscapulohumeral, congenital muscular dystrophies and the like using a combination of anti-inflammatory and nitric oxide-releasing compounds.

BACKGROUND OF THE INVENTION

The muscular dystrophies (MD) are a group of more than 30 genetic diseases characterized by progressive weakness and degeneration of the skeletal muscles that control movement. Some forms of MD are seen in infancy or childhood, while others may not appear until middle age or later. The disorders differ in terms of the distribution and extent of muscle weakness (some forms of MD also affect cardiac muscle), age of onset, rate of progression, and pattern of inheritance. Duchenne MD is the most common form of MD and primarily affects boys. It is caused by the absence of dystrophin, a protein involved in maintaining the integrity of muscle. Onset is between 3 and 5 years and the disorder progresses rapidly. Most boys are unable to walk by age 12, and later need a respirator to breathe. Girls in these families have a 50 percent chance of inheriting and passing the defective gene to their children. Boys with Becker MD (very similar to but less severe than Duchenne MD) have faulty or not enough dystrophin. Facioscapulohumeral MD usually begins in the teenage years. It causes progressive weakness in muscles of the face, arms, legs, and around the shoulders and chest. It progresses slowly and can vary in symptoms from mild to disabling. Myotonic MD is the disorder's most common adult form and is typified by prolonged muscle spasms, cataracts, cardiac abnormalities, and endocrine disturbances. Individuals with myotonic MD have long, thin faces, drooping eyelids, and a swan-like neck. Muscular dystrophies are caused by progressive degeneration of skeletal muscle fibres. Lack of one of several proteins located either at the plasma membrane [1] or, less frequently, within internal membranes [2] increases the probability of damage during contraction, and eventually leads to fibre degeneration, accompanied by severe local inflammation with infiltration of immune-competent cells [3,4]. In the most severe forms, such as Duchenne Muscular Dystrophy, regeneration is exhausted and skeletal muscle is progressively replaced by fat and fibrous tissue. This condition leads the patient to progressive weakness and eventually death by respiratory and/or cardiac failure.

The current therapeutic approaches to muscular dystrophies involve steroids, such as prednisolone and deflazacort, and dantrolene, administered in various protocols. These treatments result in modest beneficial effects and are accompanied by severe side-effects including osteoporosis, hypertension, Cushing syndrome, weight gain, cataracts, short stature, gastrointestinal symptoms, behavioural changes in the case of steroids, and liver damage with dantrolene [5-7]. With steroids, moreover there is no consensus regarding their use as standard treatment. Alternative therapeutic approaches to muscular dystrophies have been proposed, and various compounds and drugs tested. None of them has yielded favourable outcomes in clinical trials and entered the clinical practice [5].

Thus there is a need to identify therapeutic agents which slow the muscle fibre damage and delay the onset of disability in patients with muscular dystrophies more efficiently than the current therapies and causing a lesser degree of side effects. The beneficial effect of corticosteroids is believed to reside in the blocking of immune cell activation and infiltration which are precipitated by muscle fibre damage resulting from the disease [3,4]. Nitric oxide (NO) generated by a muscular NO synthase structurally and functionally linked to the dystrophin complex at the sarcolemma participates to physiological development and function of skeletal muscle. In particular it regulates excitation-contraction coupling, in such a way that it prevents the muscle from being damaged during its contractile activity. In addition, NO couples muscle function to energy availability by promoting vasodilation and thus supply of oxygen during exercise, by increasing glucose uptake in the myofibres, and by regulating the activity of enzymes relevant to cell energy metabolism [8-9].

NSAIDs are known to reduce inflammation through inhibition of cyclooxygenases 1 and 2 [10]. The authors found that the combination of nitric oxide-releasing compounds and NSAIDs is effective in retarding the development of, or reversing muscular dystrophies. Moreover these compounds, for which a novel use is proposed, are known to cause less side effects than current therapies for muscular dystrophy. They are in general well tolerated by the patients and are suitable for long-term therapies.

SUMMARY OF THE INVENTION

The present invention provides an effective and safe treatment for muscular dystrophies with less side-effects by using a combination of anti-inflammatory drugs and NO-releasing compounds.

Therefore it is an object of the present invention the use of a combination of at least one nitric oxide releasing compound and at least one anti-inflammatory compound for the preparation of a medicament or a diet supplement for the treatment or prevention of muscular dystrophy. Preferably the nitric oxide releasing compound is selected from the group of: organic nitrates, spontaneous nitric oxide donors, nitrosothiols or nitric oxide synthesis precursors. More preferably the nitric oxide synthesis precursor is L-arginine. In a preferred embodiment the nitric oxide releasing compound is selected from the group of: sodium nitroprusside, nitroglycerin, isosorbide dinitrate, isosorbide mononitrate, amyl nitrite, gallium nitrate, S-nitroso acetylpenicillamine, molsidomine, nicorandil, or derivatives thereof.

In another particular embodiment the anti-inflammatory compound is a non-steroidal anti-inflammatory compound. Preferably the non-steroidal anti-inflammatory compound is selected from the group of: salicylates and derivatives thereof, para-aminophenol derivatives, acetic acid derivatives, fenamates, propionic acid derivatives, enolic acids and derivatives thereof, pyrazolon derivatives, sulfonanilide derivatives, cyclooxygenase-2 selective inhibitors. More preferably the non-steroidal anti-inflammatory compound is selected from the group of: aspirin, salsalate, diflunisal, ibuprofen, acetaminophen, flurbiprofen, ketoprofen, piroxicam, meloxicam, nabumetone, naproxen, fenoprofen, diclofenac, indomethacin, sulindac, tolmetin, etodolac, ketorolac, oxaprozin, flufenamic acid, meclofenamate, mefenamic acid, celecoxib, valdecoxib, nimesulide, as R or S enantiomer or as racemate. These compounds can be used either as racemate or R or S enantiomer, for instance (R,S)-Flurbiprofen, (R)-Flurbiprofen, (S)-Flurbiprofen; (R,S)-Ibuprofen, (R)-Ibuprofen, (S)-ibuprofen; (R,S)-Fenoprofen, (R)-Fenoprofen, (S)-fenoprofen; (R,S)-naproxen, (R)-naproxen, (S)-naproxen; (R,S)-ketoprofen, (R)-ketoprofen, (S)-ketoprofen can be used.

It is intended by the term "derivative" any compound of the invention derived by chemical substitutions on its chemical backbone.

In a preferred embodiment the anti-inflammatory compound is a methylxanthine anti-inflammatory compound.

In another particular embodiment the nitric oxide releasing compound is isosorbide mononitrate and the anti-inflammatory compound is aspirin.

In yet another particular embodiment the nitric oxide releasing compound is isosorbide dinitrate and the anti-inflammatory compound is ibuprofen, as R or S enantiomer or as racemate.

Preferably the muscular dystrophy is selected from the group of: Duchenne muscular dystrophy, Becker muscular dystrophy, facioscapulohumeral muscular dystrophy, myotonic muscular dystrophy, limb-girdle muscular dystrophy, oculopharyngeal muscular dystrophy, Emery-Dreifuss muscular dystrophy, distal muscular dystrophy or congenital muscular dystrophy.

DETAILED DESCRIPTION OF THE INVENTION

It is an object of the present invention a pharmaceutical composition comprising a therapeutically effective amount of at least one nitric oxide releasing compound and at least one anti-inflammatory compound as defined above and suitable diluents and/or excipients and/or adjuvants and/or emollients. The pharmaceutical composition is used for the prophylaxis and/or treatment of muscular dystrophy as defined above. These pharmaceutical compositions can be formulated in combination with pharmaceutically acceptable carriers, excipients, stabilizers, diluents or biologically compatible vehicles suitable for administration to a subject (for example, physiological saline). Pharmaceutical composition of the invention include all compositions wherein said compounds are contained in therapeutically effective amount, that is, an amount effective to achieve the medically desirable result in the treated subject. The pharmaceutical compositions may be formulated in any acceptable way to meet the needs of the mode of administration. The use of biomaterials and other polymers for drug delivery, as well the different techniques and models to validate a specific mode of administration, are disclosed in literature. Any accepted mode of administration can be used and determined by those skilled in the art. For example, administration may be by various parenteral routes such as subcutaneous, intravenous, intradermal, intramuscular, intraperitoneal, intranasal, transdermal, oral, or buccal routes. Parenteral administration can be by bolus injection or by gradual perfusion over time. Preparations for parenteral administration include sterile aqueous or non-aqueous solutions, suspensions, and emulsions, which may contain auxiliary agents or excipients known in the art, and can be prepared according to routine methods. In addition, suspension of the active compounds as appropriate oily injection suspensions may be administered. Suitable lipophilic solvents or vehicles include fatty oils, for example, sesame oil, or synthetic fatty acid esters, for example, sesame oil, or synthetic fatty acid esters, for example, ethyloleate or triglycerides. Aqueous injection suspensions that may contain substances increasing the viscosity of the suspension include, for example, sodium carboxymethyl cellulose, sorbitol, and/or dextran. Optionally, the suspension may also contain stabilizers. Pharmaceutical compositions include suitable solutions for administration by injection, and contain from about 0.01 to 99 percent, preferably from about 20 to 75 percent of active compound together with the excipient. Compositions which can be administered rectally include suppositories. It is understood that the dosage administered will be dependent upon the age, sex, health, and weight of the recipient, kind of concurrent treatment, if any, frequency of treatment, and the nature of the effect desired. The dosage will be tailored to the individual subject, as is understood and determinable by one of skill in the art. The total dose required for each treatment may be administered by multiple doses or in a single dose. The pharmaceutical composition of the present invention may be administered alone or in conjunction with other therapeutics directed to the condition, or directed to other symptoms of the condition. Usually a daily dosage of active ingredients is comprised between 0.001 to 100 milligrams per kilogram of body weight. The compounds of the present invention may be administered to the patient intravenously in a pharmaceutical acceptable carrier such as physiological saline. Standard methods for intracellular delivery of peptides can be used, e.g. delivery via liposomes. Such methods are well known to those of ordinary skill in the art. The formulations of this invention are useful for parenteral administration, such as intravenous, subcutaneous, intramuscular, and intraperitoneal. As well known in the medical arts, dosages for any one patient depends upon many factors, including the patient's size, body surface area, age, the particular compound to be administered, sex, time and route of administration, general health, and other drugs being administered concurrently.

It is a further object of the present invention a diet supplement comprising an effective amount of at least one nitric oxide releasing compound and at least one anti-inflammatory compound as defined above and diluents and/or adjuvants and/or eccipients.

Another object of the invention is a method of treating or preventing muscular dystrophy comprising administering the pharmaceutical composition or the diet supplement of the invention.

BRIEF DESCRIPTION OF THE SEVERAL VIEWS OF THE DRAWINGS

The invention will be now described by means of non limiting examples referring to the following figures.

METHODS

Animal Model

The alpha-SG-null C57BL/6 mouse, one of the most severe models of muscular dystrophy was used [10,11]. In some experiments wild type (wt) C57BL/6 mouse were used as internal further control.

Drugs

Aspirin (SIGMA, A2093), Ibuprofen, (SIGMA, I7905), isosorbide-mononitrate (ISMN, Science Lab Com SLI1024), and isosorbide dinitrate (ISDN, Alexis, 400-800), Prednisolone (SIGMA, P6254).

In the in vivo experiments the drugs were administered daily in the diet to three months old animals for 30 days. The dose of aspirin was 80 mg/kg, the dose of ISMN was 35 mg/kg and that of ISDN was 10 mg/kg, while the dose of ibuprofen was 15 mg/kg. Prednisolone was used as reference drug at the dose of 2 mg/kg. When combinations of drugs were used, the drugs were both incorporated in the same diet. Control animals received the same diet without any drug incorporation.

In the in vitro experiments, the drugs were applied to satellite cells at the concentration of 100 μM for ISMN, 50 μM for ISDN, 10 μM for ibuprofen, 50 μM for aspirin and 30 μM for prednisolone. When combinations of drugs were used, the drugs were administered at the same time.

Creatine Kinase Activity Measurements

Quantitative determination of creatine kinase activity in serum of control and drug treated-animals was measured using creatine kinase reagent (Randox, CK110), according to the manufacturer's instructions. Blood was collected from tail vein and serum obtained after centrifugation at 13000 rpm for 10 minutes was stored at −80° C. before measurements [13].

Free Wheel Running

Voluntary wheel running was used as the exercise paradigm to avoid any physiological changes that may occur due to the stress of forced treadmill running. Mice were housed individually in cages equipped with a Trixie running wheel. Each wheel revolution was registered through a magnetic switch, which was connected to a counter. The number of revolutions was recorded daily for 6 days [13].

Histology

Diaphragm and tibialis anterior of untreated and drug-treated mice were isolated and included in Killik® frozen section medium, quickly frozen and cut into 8-μm thick sections with the muscle fibres oriented transversely using a cryostat. Sections were stained with either Hematoxylin&Eosin or Azan Mallory, to evaluate the number of inflammatory infiltrates and necrotic fibres (18-10 sections per tissue), respectively [10].

Cell Culture and Fusion

Satellite cells were isolated from 3-5 days old mice as described previously with some modifications [12]. In particular, after 3 days from isolation, proliferating myoblasts were harvested, counted, and plated on tissue culture plastic dishes coated with 1 mg/ml type I collagen (SIGMA, C9791). After 2 days of proliferation in growth medium, myogenic cells accounted for more than 90% of the cultures as revealed by anti-desmin immunostaining assay. Preparations showing less than 90% myogenic cells were discarded. Myoblasts were shifted to differentiating medium in the presence/absence of drugs as indicated in the Results. Growth medium contained IMDM medium supplemented with 20% Fetal Bovine Serum, 3% Chick Embryo Extract, 100 U/ml Penicillin, 100 μg/ml Streptomycin, 50 μg/ml Gentamycin. Differentiation medium contained IMDM medium supplemented with 2% Horse Serum, 100 U/ml Penicillin, 100 μg/ml Streptomycin. Fusion index was determined as the number of nuclei in sarcomeric myosin-expressing cells with more than 2 nuclei vs the total number of nuclei [10].

Statistical Analyses

Student's t test for unpaired variables (two tailed) was used. $P<0.05$ was considered significant.

Results

In Vivo Experiments

The effects of the different drugs and their combination on the number of inflammatory infiltrates, the number of necrotic fibers per section, creatine kinase activity and free wheel distance ran are shown in Table I.

TABLE I

Effect of drugs and their combination

| | Days of treatment | Histology data | | CK level (U/l) | Free wheel test (km/24 h) |
| | | N° of inflammatory infiltrates/sections | N° of necrotic fibres/section | | |
|---|---|---|---|---|---|
| Control | 30 | 195.2 ± 41.5 | 272.2 ± 37.0 | 970 ± 86 | 0.13 ± 0.02 |
| Aspirin | 30 | 122.2 ± 17.1° | 249.0 ± 32.1 | 841 ± 33 | 0.15 ± 0.02 |
| Ibuprofen | 30 | 116.1 ± 11.1° | 269.0 ± 34.3 | 851 ± 41 | 0.12 ± 0.01 |
| ISMN | 30 | 190.2 ± 33.2 | 238.0 ± 27.2 | 787 ± 33 | 0.18 ± 0.03 |
| ISDN | 30 | 180.2 ± 18.2 | 248.0 ± 12.1 | 737 ± 45 | 0.15 ± 0.02 |
| Aspirin plus ISMN | 30 | 88.2 ± 10.5*+ | 46.3 ± 2.8*+§ | 472.7 ± 48.9*+§ | 0.77 ± 0.1*+§ |
| ISDN plus ibuprofen | 30 | 80.2 ± 6.5*+ | 38.3 ± 2.8*+§ | 389.7 ± 19.1*+§ | 0.84 ± 0.2*+§ |
| Prednisolone | 30 | 103.4 ± 12.0* | 217.3 ± 37.3* | 757.6 ± 37.5 | 0.38 ± 0.1* | n = 4 in each group.
*$P < 0.01$;
°$P < 0.05$ vs control;
+$P < 0.05$ vs aspirin or ibuprofen;
§$P < 0.05$ vs prednisolone, wt mice: 2.1 ± 0.3 Km/24 h in the free wheel run test.
CK level values in wt animals were 82 ± 7.5

The authors found that administration of aspirin, ibuprofen, ISMN and ISDN alone did not have significant effects on any of the parameters measured.

By contrast, the combination of aspirin and ISMN and the combination of ibuprofen and ISDN, were significantly effective in reducing the histological, functional and biochemical alterations observed in these animals (Table I and FIGS. 1-5).

In particular, serum levels of creatine kinase, a hallmark of muscle damage, were significantly lower in combination-treated animals (Table I, FIG. 1) when compared to control animals receiving the diet without any drug incorporation. Consistently, animals treated by drug combination performed significantly better on the free-wheel running test (Table I, FIG. 2) when compared to control and prednisolone-treated animals. In addition, the combined treatment aspirin plus ISMN and ibuprofen plus ISDN treatments on the free-wheel running test improved significantly free wheel running when compared to the reference compound prednisolone.

Figure 1:
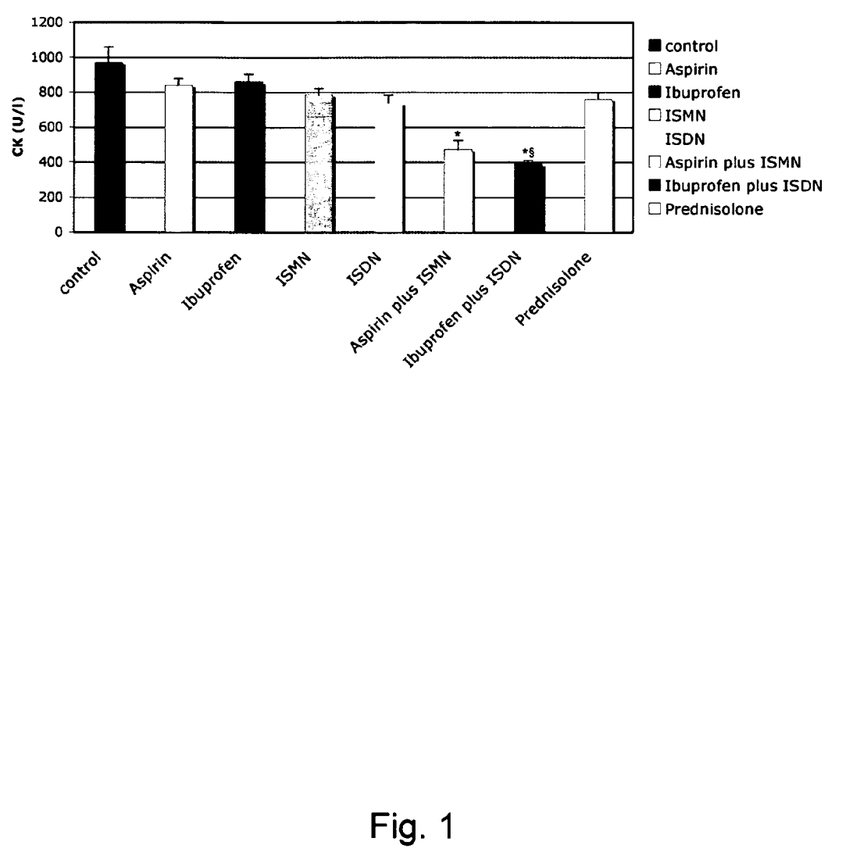
FIG. 1: alpha-sarcoglycan (SG)-null C57BL/6 mice were treated for 30 days with the indicated drugs, or combinations of drugs incorporated into the diet as described in the Methods. Serum creatin kinase (CK) concentrations were measured from mouse blood samples obtained by tail vein withdrawal using the indirect colorimetric assay (Roche Diagnostics), following standard procedures. Values shown are the results of 4 experiments ±S.E.M. *$P<0.01$ vs untreated α-SG null control mice; § $P<0.05$ vs prednisolone-treated α-SG null mice.
Figure 2:
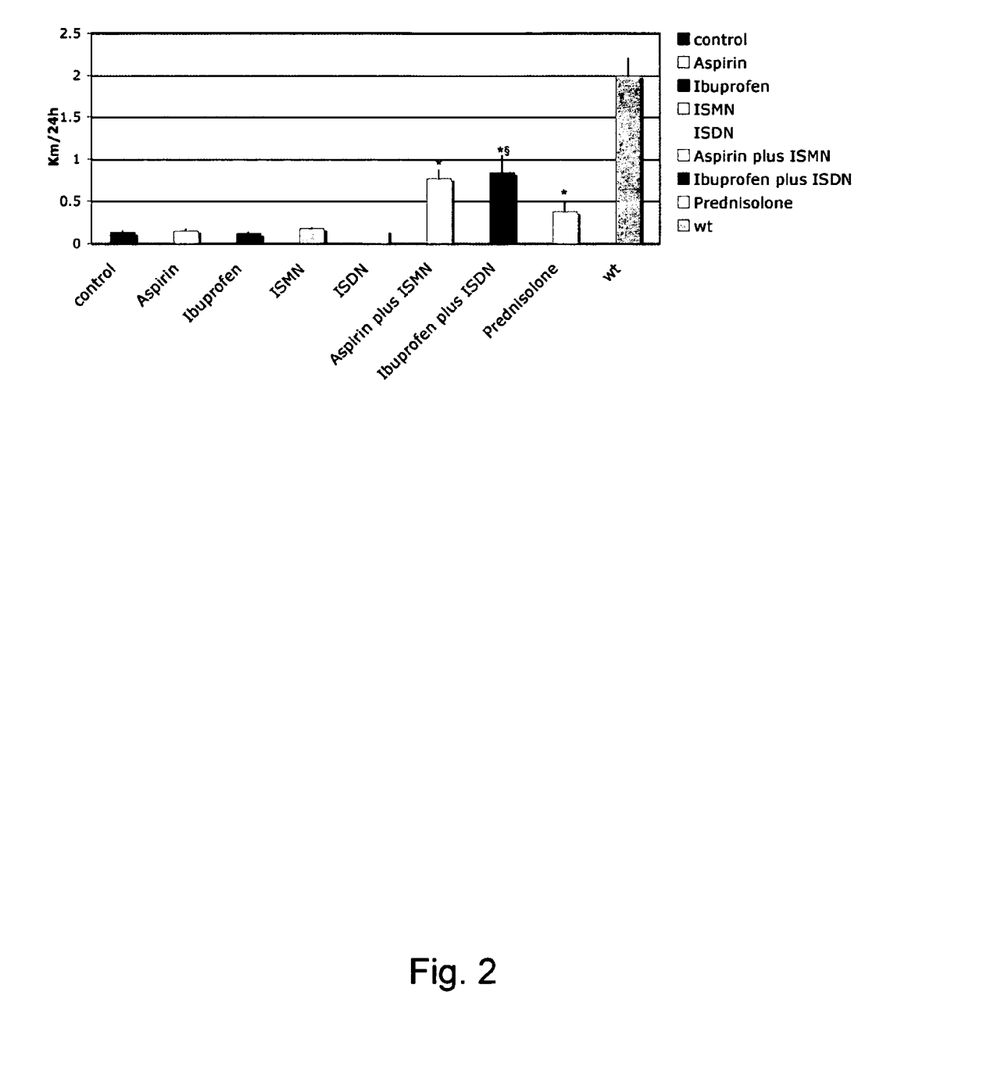
FIG. 2: alpha-SG-null C57BL/6 mice were treated for 30 days with the indicated drugs, or combinations of drugs incorporated into the diet as described in the Methods. Locomotor performance was measured through the Running Wheel Activity, to this end mice were housed individually in cages equipped with a Trixie running wheel. Each wheel revolution was registered through a magnetic switch, which was connected to a counter. The number of revolutions was recorded daily for 6 days. Values shown are the results of 4 experiments ±S.E.M. *$P<0.01$ vs untreated α-SG null control mice; § $P<0.05$ vs prednisolone-treated α-SG null mice. The results of 9 experiments ±S.E.M of Running Wheel Activity measured in wild type (wt) C57BL/6 mice are also reported.
Figure 3:
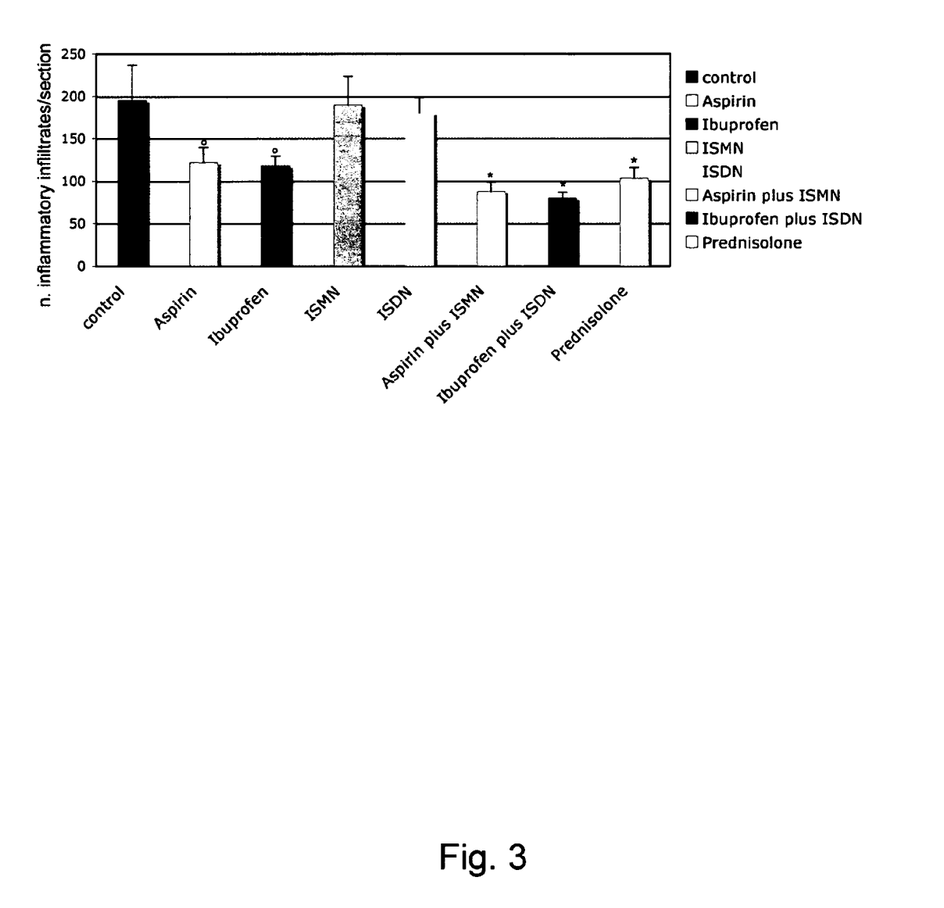
FIG. 3: alpha-SG-null C57BL/6 mice were treated for 30 days with the indicated drugs, or combinations of drugs incorporated into the diet as described in the Methods. Tibialis anterior muscles were dissected and frozen in liquid nitrogen-cooled isopentane. The number of inflammatory infiltrates was measured on Azan-Mallory-stained serial muscle sections. Values shown are the results of 4 experiments ±S.E.M. *$P<0.01$ and °$P<0.05$ vs untreated α-SG null control mice.
Figure 5:
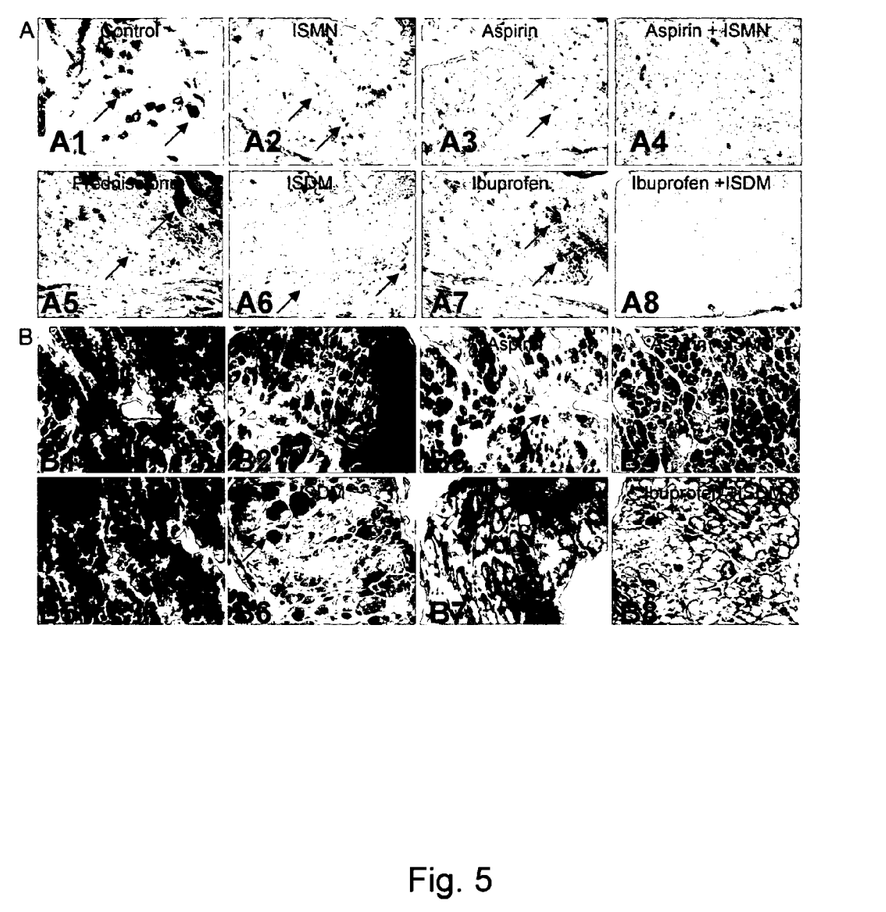
FIG. 5: alpha-SG-null C57BL/6 mice were treated for 30 days with the indicated drugs, or combinations of drugs incorporated into the diet as described in the Methods. Shown are representative histological images of diaphragm muscles cross cryosections stained with in hematoxilin & eosin (A) or Azan Mallory (B) obtained as described in FIGS. 4 and 3, respectively. Arrows in panels A1-8 point to fiber necrosis, arrows in panels B1-8 point to inflammatory infiltrates.

Moreover, animals treated with the drug combinations showed significantly reduced inflammatory infiltrates (Table I and FIG. 3, FIG. 5).

Figure 4:
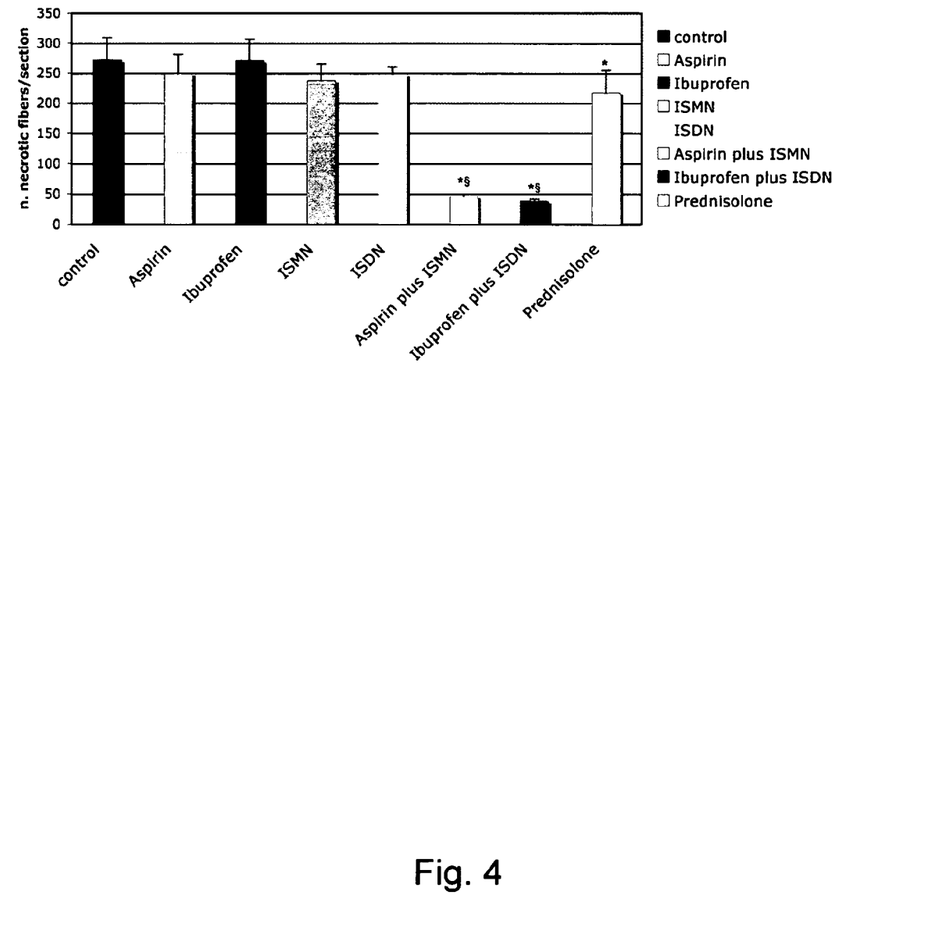
FIG. 4: alpha-SG-null C57BL/6 mice were treated for 30 days with the indicated drugs, or combinations of drugs incorporated into the diet as described in the Methods. Diaphragm muscles were dissected, frozen in liquid nitrogen-cooled isopentane and stained with hematoxilin & eosin according to standard procedures. Shown are the numbers of necrotic and centronucleated fibers in 4 animals per group ±S.E.M. *$P<0.01$ vs untreated α-SG null control mice; § $P<0.05$ vs prednisolone-treated α-SG null mice.

In addition, fibre necrosis was almost undetectable in animals treated with drug combinations (Table I and FIG. 4, FIG. 5). FIG. 5 reports representative images showing the reduction in inflammatory infiltrates (panels B1-8) and fibre necrosis (panel A1-8) induced by the drug combinations as indicated by the arrows.

In Vitro Experiments

Satellite cells isolated from newborn alpha-SG-null C57BL/6 mice and plated at low density ($6 \times 10^3$ cells/cm$^2$) were maintained for 48 h in growth medium, and then switched to the differentiating medium in the presence or absence of ISMN, ISDN, aspirin, ibuprofen, ISMN plus aspirin or ISDN plus ibuprofen. The fusion index was measured after 48 and 72 h, results are shown Table II AND FIG. 6.

TABLE II

Effect of drugs and their combination on fusion index in satellite cells

| | hours of treatment | Fusion index (%) |
|---|---|---|
| Control | 48 | 21 ± 1.3 |
| (n = 4) | 72 | 45 ± 2.5 |
| aspirin | 48 | 20 ± 1.9 |
| (n = 4) | 72 | 43 ± 1.7 |
| Ibuprofen | 48 | 21 ± 1.2 |
| (n = 4) | 72 | 42 ± 2.3 |
| ISMN | 48 | 41 ± 2.2*§ |
| (n = 4) | 72 | 76 ± 3.3*§ |
| ISDN | 48 | 41 ± 2.1*§ |
| (n = 4) | 72 | 76 ± 3.1*§ |
| Aspirin plus ISMN | 48 | 52 ± 3.1*°§ |
| (n = 4) | 72 | 93 ± 4.6*°§ |
| Ibuprofen plus ISDN | 48 | 55 ± 2.0*°§ |
| (n = 4) | 72 | 102 ± 4.9*°§ |
| Prednisolone | 48 | 18 ± 0.9 |
| (n = 4) | 72 | 41 ± 2.0 |

Figure 6:
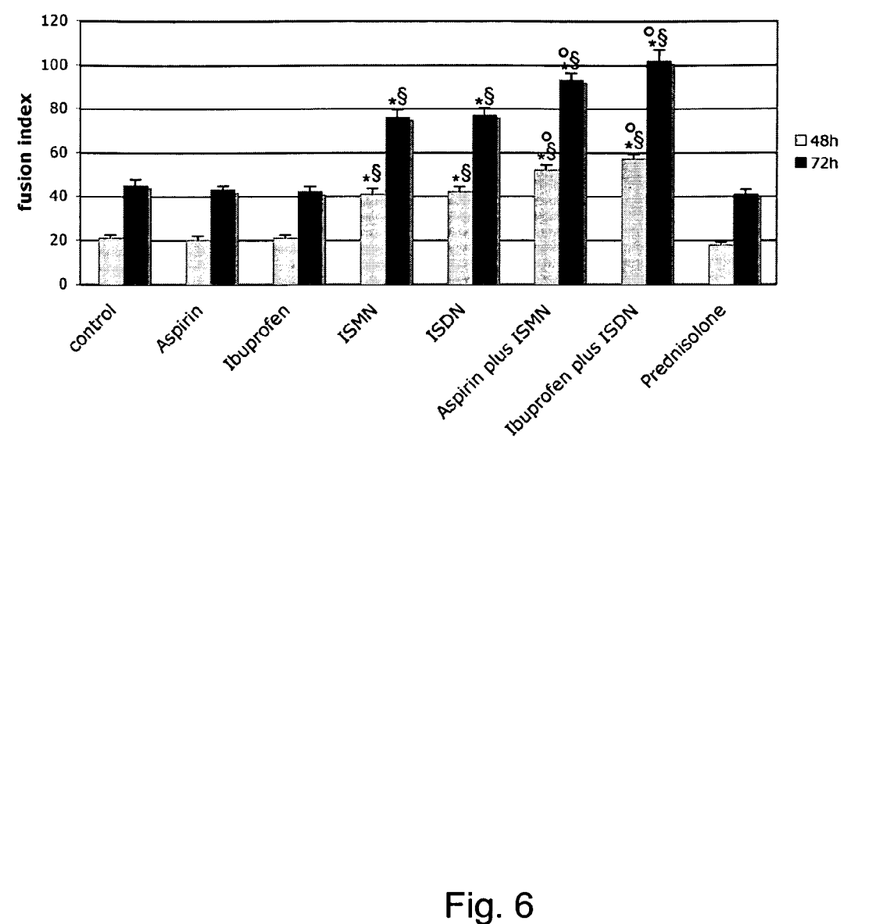
FIG. 6: Satellite cells from alpha-SG-null C57BL/6 mice were isolated from 3-5 days old mice and induced to differentiate in the presence of the indicated drugs as described in the methods. Fusion index was determined at 48 and 72 h as the number of nuclei in sarcomeric myosin-expressing cells with more than 2 nuclei vs the total number of nuclei. Reported are the results ±S.E.M in 4 experiments. *$P<0.01$ and °$P<0.05$ vs untreated α-SG null control mice, § $P<0.05$ vs prednisolone-treated α-SG null mice.

*$P < 0.01$ vs control;
°$P < 0.05$ vs ISMN or ISDN,
§$P < 0.01$ vs prednisolone The authors found that the combinations of aspirin and ISMN and of ibuprofen and ISDN significantly increased the fusion index when compared to control cells (Table II and FIG. 6). ISMN and ISDN were effective on their own but less than when combined with aspirin or ibuprofen (statistical significance values: *$P<0.01$ vs control; °$P<0.05$ vs ISMN or ISDN). ISMN and ISDN alone or combined with aspirin and ibuprofen yielded fusion index values significantly greater than those obtained with prednisolone (§$P<0.01$ vs prednisolone). To observe an enhanced satellite fusogenic properties is relevant in the therapeutic perspective to muscular dystrophies since enhanced fusion of satellite cells to damaged fibers implies a faster and more efficient repair of dystrophic damaged fibers.

Bibliography

[1] Blake D J, Weir A, Newey S E, Davies K E. (2002) *Physiol. Rev.* 82, 291-329.
[2] Nishino, I. and Ozawa, E. (2002) *Curr. Opin. Neurol.* 15, 539-544.
[3] Burton, E. A. and Davies, K. E. (2002) *Cell* 108, 5-8.
[4] Emery, A. E. (2002) *Lancet* 317, 991-995.
[5] Skuk, D., Vilquin, J. T. and Tremblay, J. P. (2002) *Curr. Opin. Neurol.* 15, 563-569.

[6] Bertorini, T. E., Palmieri, et al., (1991) *Muscle Nerve.* 14, 503-507.
[7] Mendell, J. R., Moxley, R. T., et al., (1989) *N. Engl. J. Med.* 320, 1592-1597
[8] Stamler, J., and Meissner, G. (2001) *Physiol. Rev.* 81, 209-237.
[9] Nisoli, E., Clementi, E., et al., (2003) *Science* 299, 896-899.
[10] Sampaolesi, M., Torrente, et al., (2003) *Science* 301, 487-492
[11] Duclos F, Straub V, et al., (1998) *J. Cell Biol.* 142, 1461-1471.
[12] Cossu, G., B. Zani, et al., (1980) *Cell Differ.* 9, 357-368.
[13] Brunelli, S., Sciorati, C., et al., (2007) *PNAS,* 104, 264-269.

The invention claimed is:

1. A method of treating muscular dystrophy comprising administering an effective amount of a combination of isosorbide mononitrate and aspirin or an effective amount of a combination of isosorbide dinitrate and ibuprofen to a patient in need thereof, and wherein the ibuprofen comprises an R or S enantiomer or is a racemate.

2. The method according to claim 1 wherein the muscular dystrophy is selected from the group consisting of Duchenne muscular dystrophy, Becker muscular dystrophy, facioscapulohumeral muscular dystrophy, myotonic muscular dystrophy, limb-girdle muscular dystrophy, oculopharyngeal muscular dystrophy, Emery-Dreifuss muscular dystrophy, distal muscular dystrophy and congenital muscular dystrophy.

3. A method of treating muscular dystrophy comprising administering the pharmaceutical composition comprising an effective amount of a combination of isosorbide mononitrate and aspirin or an effective amount of a combination of isosorbide dinitrate and ibuprofen, wherein the ibuprofen comprises an R or S enantiomer or is a racemate, and diluents and/or emollients and/or adjuvants and/or excipients.

4. The method of claim 1 comprising administering an effective amount of a combination of isosorbide mononitrate and aspirin.

5. The method of claim 1 comprising administering an effective amount of a combination of isosorbide dinitrate and ibuprofen to a patient in need thereof, and wherein the ibuprofen comprises an R or S enantiomer or is a racemate.

* * * * *